United States Patent [19]
Packard et al.

[11] 3,965,144
[45] June 22, 1976

[54] CARBANILATE COMPOUND FOR ERYTHEMAL PROTECTION

[75] Inventors: Martin E. Packard, Los Altos Hills; Edwin F. Ullman, Atherton; Terry L. Burkoth, Palo Alto, all of Calif.

[73] Assignee: Syva Company, Palo Alto, Calif.

[22] Filed: Oct. 10, 1973

[21] Appl. No.: 405,237

Related U.S. Application Data

[63] Continuation-in-part of Ser. No. 388,004, Aug. 13, 1973, abandoned, which is a continuation of Ser. No. 71,783, Sept. 14, 1970, abandoned.

[52] U.S. Cl. ................... 260/471 C; 204/158 R; 260/471 R; 260/472; 260/518 R; 260/613 D; 424/60
[51] Int. Cl.² ............................. C07C 125/06
[58] Field of Search............ 260/471 C, 472; 424/60

[56] References Cited
UNITED STATES PATENTS
3,790,615  2/1974  Traber et al. .................... 260/471 C Primary Examiner—Richard L. Raymond
Attorney, Agent, or Firm—Townsend and Townsend

[57] ABSTRACT

Compounds are provided for reducing erythemal response which are photoreactive precursors to para-aminobenzoic acid or its physiologically acceptable esters. Upon exposure to ultraviolet radiation of greater than about 280nm, the compounds of this invention undergo a photoreactive degradation to provide a regulated amount of a sunscreen material which screens out ultraviolet radiation which could lead to erythema.

The compounds are benzyl esters of p-carboxycarbanilic acid and the dermatological and physiological acceptable esters of the carboxy group.

8 Claims, No Drawings

CARBANILATE COMPOUND FOR ERYTHEMAL PROTECTION

CROSS REFERENCE TO RELATED APPLICATIONS

This application is a continuation-in-part of application Ser. No. 388,004 filed on Aug. 13, 1973, now abandoned, which in turn was a continuation of application Ser. No. 71,783, filed Sept. 14, 1970, which was abandoned concurrently with the filing of the aforementioned application.

BACKGROUND OF THE INVENTION

Field of the Invention

Because of the wide exposure of human epidermis to sunlight for cosmetic reasons or as an employment environment, numerous compositions have been developed which protect the skin from the painful erythemal response. The primary materials which are used are either ultraviolet absorbers (sunscreens) and/or ultraviolet scatterers. With both of these materials, the skin is substantially prevented from tanning or burning while there is a sufficient amount of the material present, but remains unprotected once the material has been removed. Therefore, tanning occurs as a result of partial or no protection during the periods when insufficient amounts or none of the sunscreen is available.

It would be desirable to have a compound which would provide a degree of regulated protection. That is, a compound which will increase the amount of protection as the amount of sunlight intensity increased. Also, higher substantivity is desirable. By substantivity is intended retention of the material by the skin during normal usage of the sunscreen. Also, it is of value to provide compounds which allow for greater synthetic flexibility in varying the compounds as to their lipophilic/hydrophilic balance (HLB) to allow for greater flexibility in preparing formulations for application to the skin, such as solutions, creams, ointments, aerosols and the like.

SUMMARY OF THE INVENTION

Method, compounds and formulations are provided to produce a regulated erythemal response to exposure of the epidermis to ultraviolet radiation. The compounds are alkoxybenzyl p-carboxycarbanilate esters, where the carboxy group may be the parent acid or its dermatologically and physiologically acceptable esters. The carboxy esters are normally alkyl or substituted alkyl. The compounds when applied to the epidermis in an acceptable vehicle undergo by virtue of a photoreaction a cleavage to produce the sunscreen compound, p-aminobenzoic acid or its correlated ester.

DESCRIPTION OF THE SPECIFIC EMBODIMENTS

The compounds employed in this invention are alkoxybenzyl p-carboxycarbanilate esters, where the carboxy group may be the parent acid or alkyl or substituted alkyl esters thereof. The compounds will normally be of from 17 to 38 carbon atoms, more usually of from 17 to 30 carbon atoms, having from 7 to 16, more usually from 7 to 12 heteroatoms, which are oxygen, sulfur or nitrogen, preferably oxygen and nitrogen (atomic number 7 to 8) and usually having from 1 to 2 nitrogen atoms, and from 6 to 14 oxygen atoms, usually from 6 to 10 oxygen atoms. The compounds will usually normally be free of aliphatic unsaturation.

For the most part, the compounds of this invention will have the following formula:

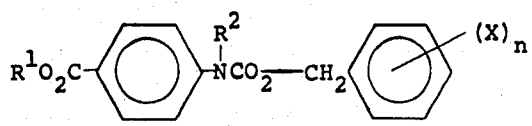

wherein:

$R^1$ is hydrogen, saturated aliphatic, e.g. alkyl or substituted alkyl, usually of from 1 to 18 carbon atoms, more usually of from 1 to 8 carbon atoms, and preferably of from 1 to 6 carbon atoms and having from 0 to 8 heteroatoms (at least 1 heteroatom when substituted alkyl), usually from 0 to 3 heteroatoms, and preferably from 0 to 2 heteroatoms, which are oxygen, sulfur or nitrogen, preferably oxygen and nitrogen, and particularly preferred oxygen as oxy (hydroxyl or ether);

$R^2$ is hydrogen or saturated aliphatic, e.g. alkyl, usually of from 1 to 12 carbon atoms, more usually of from 1 to 8 carbon atoms, and preferably of from 1 to 6 carbon atoms, and preferably hydrogen;

$n$ is an integer of from 2 to 3, preferably 2; and

X is alkoxy of from 1 to 18 carbon atoms, more usually of from 1 to 12 carbon atoms, preferably of from 1 to 3 carbon atoms, and particularly preferred methyl, wherein usually not more than one X is in the ortho position.

Preferred compounds of this invention have the following formula:

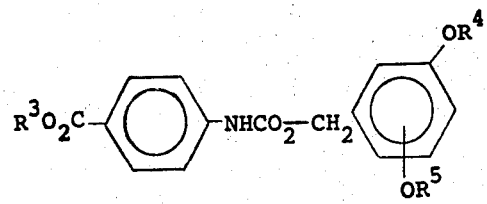

wherein:

$R^3$ is hydrogen, alkyl or substituted alkyl of from 1 to 8 carbon atoms, more usually of from 1 to 6 carbon atoms, and preferably of from 1 to 4 carbon atoms having from 0 to 2 heteroatoms (1 heteroatom when substituted alkyl) which are of atomic number 7 to 8 (oxygen or nitrogen), particularly oxygen as oxy; and $R^4$ and $R^5$ are the same or different and are alkyl of from 1 to 6 carbon atoms, usually of from 1 to 3 carbon atoms, and preferably methyl.

Compounds within this invention include:

3,4,5-trimethyoxybenzyl p-carboxycarbanilate 3,4,5-triethoxybenzyl N-methyl p(methoxycarbonyl)-carbanilate 3,5-diethoxybenzyl p-(2'-hydroxyethoxycarbonyl)carbanilate 2-methoxy-5-decyloxybenzyl p-(2'-propoxyethoxycarbonyl)carbanilate 3,5-dimethoxybenzyl p-(2'-(2''-hydroxyethoxy)ethoxycarbonyl)carbanilate 2,5-diethoxybenzyl p-(2'-dimethylaminoethoxycarbonyl)carbanilate 2-methoxy-5-hexadecyloxybenzyl p-carboxycarbanilate 3,5-dimethoxybenzyl p-(O¹-glycerylcarbonyl)carbanilate 3,5-dimethoxybenzyl N-ethyl p-(O¹-glycerylcarbonyl)carbanilate 3,5-dimethoxybenzyl p-(2'-ethoxyethoxycarbonyl)carbanilate 2,5-diethoxybenzyl N-methyl p-(ethoxycarbonyl)carbanilate 2,5-dimethoxybenzyl N-ethyl p-(isopentoxycarbonyl)carbanilate 2,5-dimethoxybenzyl p-(methoxytetraethyleneoxycarbonyl)carbanilate 2,5-dimethoxybenzyl p-(ethoxyhexaethyleneoxycarbonyl)carbanilate 2-methoxy-5-dodecyloxy p-(methoxydiethyleneoxycarbonyl)carbanilate The compounds of this invention when subjected to sunlight or ultraviolet light in the range of 280 to 320nm undergo a photoreaction as follows:

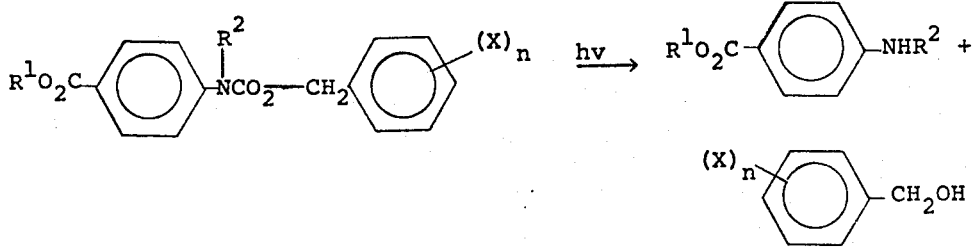

The resulting p-aminobenzoic acid or derivative thereof acts as a sunscreen. The compounds of this invention will normally not absorb significant light above 280nm, so that the tanning radiation from sunlight is effective while the concentration of the sunscreen compound is being built up in accordance with the intensity of the light.

In employing the sunscreen compounds of this invention, a suitable vehicle will normally be employed. Various physiological and dermatological solvents may be used such as isopropyl alcohol, ethyl alcohol, glycerol, and the like. Normally, the formulation will include other ingredients, and the photoreactive compound may be present in a cream, lotion, aerosol, ointment, or the like.

A typical formulation could be in percent by weight, 5% photoreactive precursor, 5% water soluble lanolin, 50% ethyl alcohol, 40% butyl oleate, and minor amounts of perfume, colorants and the like. Examples of other lotions may be found in U.S. Pat. No. 3,175,950.

The lotions generally contain a film forming base, a solvent, and the effective compound. For creams, normally a film forming base (preferably water insoluble), an emulsifier, a stabilizer, water and the effective compound are employed. For a heavy lotion, the ingredients employed in a cream will be present in somewhat smaller proportion to provide the desired viscosity.

The amount of photoreactive precursor will normally be at least about 0.5 and normally not exceeding 20 wt. % of the formulation, more usually being in the range of about 1 to 10 wt. % in the formulation.

The following examples are offered by way of illustration and not by way of limitation.

(All temperatures not otherwise indicated are in centigrade).

Example I. 2,5-dimethoxybenzyl p-carboxycarbanilate

A 50% solution of 2,5-dimethoxybenzyl alcohol and dry benzene was added dropwise to an ice-cold stirring solution of 12.5 wt. % phosgene in benzene (1 mole of alcohol per 2 moles phosgene). The resulting solution was maintained at 0° for 1 hour and then stirred an additional 2 hours at room temperature. Excess phosgene, byproduct hydrogen chloride and a small amount of benzene was removed in vacuo at room temperature to provide crude 2,5-dimethoxybenzyloxycarbonyl chloride solution. The crude product was added dropwise to a 50 wt. % solution of p-aminobenzoic acid in dry tetrahydrofuran containing 2 moles of pyridine per mole of acid. An additional two equivalents of pyridine was added dropwise simultaneously with the carbonyl chloride addition. Upon completion of the addition (25–40 mins.), the resulting mixture was added dropwise with stirring to ice-cold 5% aqueous hydrochloric acid (10 volumes of acid per final volume of reaction solution). The product was collected by filtration, dried and purified by recrystallization from acetone. m.p. 124–25.

Example II. 2,5-dimethoxybenzyl p-ethoxycarbonyl(carbanilate

To a stirring 10 wt. % solution of the product of Example I in dry tetrahydrofuran (THF) was added in one portion at room temperature 1.3 mole equivalents of oxalyl chloride. Several drops of dry methylformamide were then added to initiate the reaction. After stirring for 30 minutes at room temperature, the reaction solution was slightly yellow and gas evolution had ceased. To the solution was then added dropwise with stirring at room temperature, 1.1 mole equivalent of absolute ethanol in 4 equivalents of dry pyridine. After stirring for one hour, the solution was diluted with ether and washed exhaustively with water. The ethereal solution was then washed twice with 1N sodium hydroxide, once with 1N hydrochloric acid, followed by water and finally saturated aqueous sodium bicarbonate. Upon concentration in vacuo, a clear oil was obtained which crystallized upon scratching with the addition of aqueous methanol. The product was filtered and purified by recrystallization from aqueous methanol. m.p. 121°–2°.

Example III. 2,5-dimethoxybenzyl p-(O¹-glycerylcarbonyl)carbanilate

To 13.8g (0.042 mole) of the compound of Example I in 100ml of dry tetrahydrofuran was added 5.7g (0.045 mole) of oxalyl chloride. A few drops of dimethylformamide were added to initiate the reaction. After 0.5 hour, the acid chloride solution was added dropwise to a cold stirred solution of the acetonide of glycerol (6g, 0.045 mole) in 65ml of dry pyridine. After completion of the addition, the mixture was stirred at room temperature for 1.5 hour. The reaction mixture was then added to ice water and the product extracted with ether. The ethereal solutions were washed with 1N, HCl, 1N sodium hydroxide, and with several portions of water. The ether was then dried with magnesium sulfate and evaporated in vacuo to yield 16.5g of a crude product. The crude product was purified employing a silica gel column, eluting with ether, hexane, 1:1 and isolating the product in the first fractions. Weight 12.3g, m.p. 83°–85°.

The above product (1.0g, 0.0023 mole) in 5ml methoxyethanol was treated with 1.36g (0.02 mole) of boric acid and the mixture stirred while heated in a boiling water bath for 0.5 hour. To the mixture was then added 100ml of ether and the mixture extracted with 3 portions of water, 50ml each. A solid separated at the ether-water interface which was collected. Weight 500mg, m.p. 155°.

Example IV. 3,5-dimethoxybenzyl N-ethyl p-(methoxycarbonyl)carbanilate 3,5-dimethoxybenzyl p-carboxycarbanilate was prepared in the same manner as provided in Example I, except that 3,5-dimethoxybenzyl alcohol was employed instead of 2,5-dimethoxybenzyl alcohol.

A solution-suspension of 3,5-dimethoxybenzyl p-carboxycarbanilate (454mg, 1.37 mmole) in 20ml of dry xylene was refluxed with 250mg of sodium hydride for 20 hours under nitrogen. The reaction mixture was cooled slightly and 10ml of ethyl bromide over molecular sieves 3A) was added by syringe. Refluxing was then maintained for 10 hours, at which time the reaction mixture was cooled, diluted with water, and extracted four times with ether. After acidifying the mixture with concentrated hydrochloric acid, the mixture was extracted six times with 25ml aliquots of ether. The NMR in $D_6$ acetone showed a complex mixture, with some of the desired product of ethyl incorporation.

The material was dissolved in methanol and esterified according to conventional procedures with excess ethereal diazomethane. The product was then chromatographed with thin layer chromatography employing benzene:chloroform:ethyl acetate-100:100:10. The main spot was extracted to give an oil which was the desired product. Approximately 50mg.

Preliminary photolysis of the product showed approximately the same efficiency as the compound free of the nitrogen alkyl substituent.

Example V. 2-Ethoxy-ethyl N-(2,5-dimethoxy-benzyloxycarbonyl)-para-aminobenzoate A solution of N-(2,5-dimethoxybenzyloxy-carbonyl)-para-aminobenzoic acid (3.31g) in dry THF (30ml) was treated with oxalyl chloride (1.65g) and one drop of dry DMF. After 0.5 hour the reaction had subsided and the acid chloride solution was added dropwise to a stirred solution of ethoxyethanol (1.2g) in dry pyridine, then poured into water (ca 250ml) and the crude product extracted into ether. The ether was washed with 1N HCl 1N NaOH, water and dried with Mg $SO_4$. The solvent was concentrated in vacuo leaving a yellow oil.

The oil was dissolved in ca 75ml 95% ethanol, filtered free of insoluble material and treated with water until cloudy. The product (2.0g) separated as needles. m.p. 90°–92°.

The compounds of this invention find particular value in providing a regulated protection against erythemal response. By being photoreactive and undergoing a photoreaction which results in the formation of a sunscreen, the amount of sunscreen is proportional to the amount of erythema producing light. Furthermore, the precursors which are photoreactive do not have significant absorption in the erythema producing range of wavelengths, so that the skin is permitted to tan as the amount of sunscreen builds up. In addition, the portion of the molecule which is lost and does not provide the sunscreen can be widely varied so as to provide desirable properties to the original compound, without affecting the properties of the sunscreen. This can aid in formulation and in allowing for a wider variety of esters, since the effect of the ester group on the compound's physical and chemical properties, can be accentuated or compensated for by substituents on the portion of the molecule which does not provide the sunscreen.

The subject compositions can be used with mammals, both people and animals, where protection from erythemal response is desired. The compounds are easily formulated in conventional formulations, which can be used to enhance substantivity.

Although the foregoing invention has been described in some detail by way of illustration and example for purposes of clarity of understanding, it will be obvious that certain changes and modifications may be practiced within the scope of the appended claims.

What is claimed is:
1. A compound of the formula

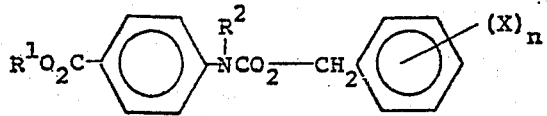

wherein $R^1$ is hydrogen or saturated aliphatic of from 1 to 6 carbon atoms and 0 to 3 heteroatoms, which are oxygen, as hydroxyl or ether oxygen;
$R^2$ is hydrogen or saturated aliphatic of from 1 to 6 carbon atoms;
$n$ is an integer of from 2 to 3; and
X is alkoxy of from 1 to 3 carbon atoms.
2. A compound according to claim 1, wherein $R^1$ is hydrogen.
3. A compound of the formula

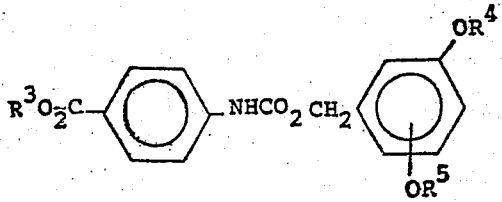

wherein $R^3$ is hydrogen, alkyl or substituted alkyl of from 1 to 6 carbon atoms and from 0 to 2 heteroatoms which are oxygen as hydroxyl or ether oxygen;
$R^4$ and $R^5$ are the same or different and are alkyl of from 1 to 3 carbon atoms.
4. A compound according to claim 3, wherein $R^3$ is hydrogen.
5. A compound according to claim 3, wherein $R^3$ is alkyl.
6. A compound according to claim 3, wherein $R^3$ is substituted alkyl having from 1 to 2 oxygen atoms.
7. 2,5-dimethoxybenzyl p-carboxycarbanilate.
8. 2-Ethoxy-ethyl N-(2,5-dimethoxy-benzyloxycarbonyl)-para-aminobenzoate.

* * * * *